United States Patent [19]
Wallin et al.

[11] Patent Number: 5,255,073
[45] Date of Patent: Oct. 19, 1993

[54] APPARATUS FOR EMITTING AND RECEIVING LIGHT

[75] Inventors: Svante Wallin, Lund; Leif Unéus, Malmö, both of Sweden

[73] Assignee: OPSIS AB, Furulund, Sweden

[21] Appl. No.: 775,983

[22] PCT Filed: May 18, 1990

[86] PCT No.: PCT/SE90/00334
§ 371 Date: Nov. 19, 1991
§ 102(e) Date: Nov. 19, 1991

[87] PCT Pub. No.: WO90/14581
PCT Pub. Date: Nov. 29, 1990

[30] Foreign Application Priority Data
May 19, 1989 [SE] Sweden .................. 8901808

[51] Int. Cl.$^5$ .................................. G01J 3/42
[52] U.S. Cl. ........................ 356/437; 250/573; 359/858
[58] Field of Search .......... 356/437, 438, 439; 250/338.5, 216, 221, 573; 359/858

[56] References Cited
U.S. PATENT DOCUMENTS

| | | |
|---|---|---|
| 2,930,893 | 3/1960 | Carpenter et al. |
| 3,474,252 | 10/1969 | Jacobsen .............. 250/221 |
| 3,558,894 | 1/1971 | Odone et al. .......... 250/216 |
| 3,768,908 | 10/1973 | Zaromb . |
| 3,885,162 | 5/1975 | Geertz ................. 356/439 |
| 4,247,770 | 1/1981 | Welch . |
| 4,555,627 | 11/1985 | McRae, Jr. . |
| 4,790,652 | 12/1988 | Unéus et al. . |

FOREIGN PATENT DOCUMENTS 1623527 4/1971 Fed. Rep. of Germany .
2381320 9/1978 France .

Primary Examiner—Richard A. Rosenberger

[57] ABSTRACT

An apparatus for emitting and receiving light comprises an emitter, which consists of a light source (5) and a concave mirror (7), and a receiver which receives light from the emitter and which is connected to analyzing equipment (3). Furthermore, the receiver comprises a concave mirror (9) which is disposed behind the mirror (7) of the emitter and whose diameter is larger than that of the mirror (7) of the emitter and whose focus is located in front of the light source (5). In the focus of the mirror (9) is positioned one end of an optical fibre (19) for transmitting the received light to the analyzing equipment (3). Moreover, the apparatus comprises a retroreflector unit (17) for reflecting the light from the emitter to the receiver, and a movable shielding element (11) which is provided between the light source (5) and the optical fibre (19) and which prevents, in a first position, the light from the light source from reaching the optical fibre directly, and lets through, in a second position, the light from the light source directly to the optical fibre.

4 Claims, 1 Drawing Sheet

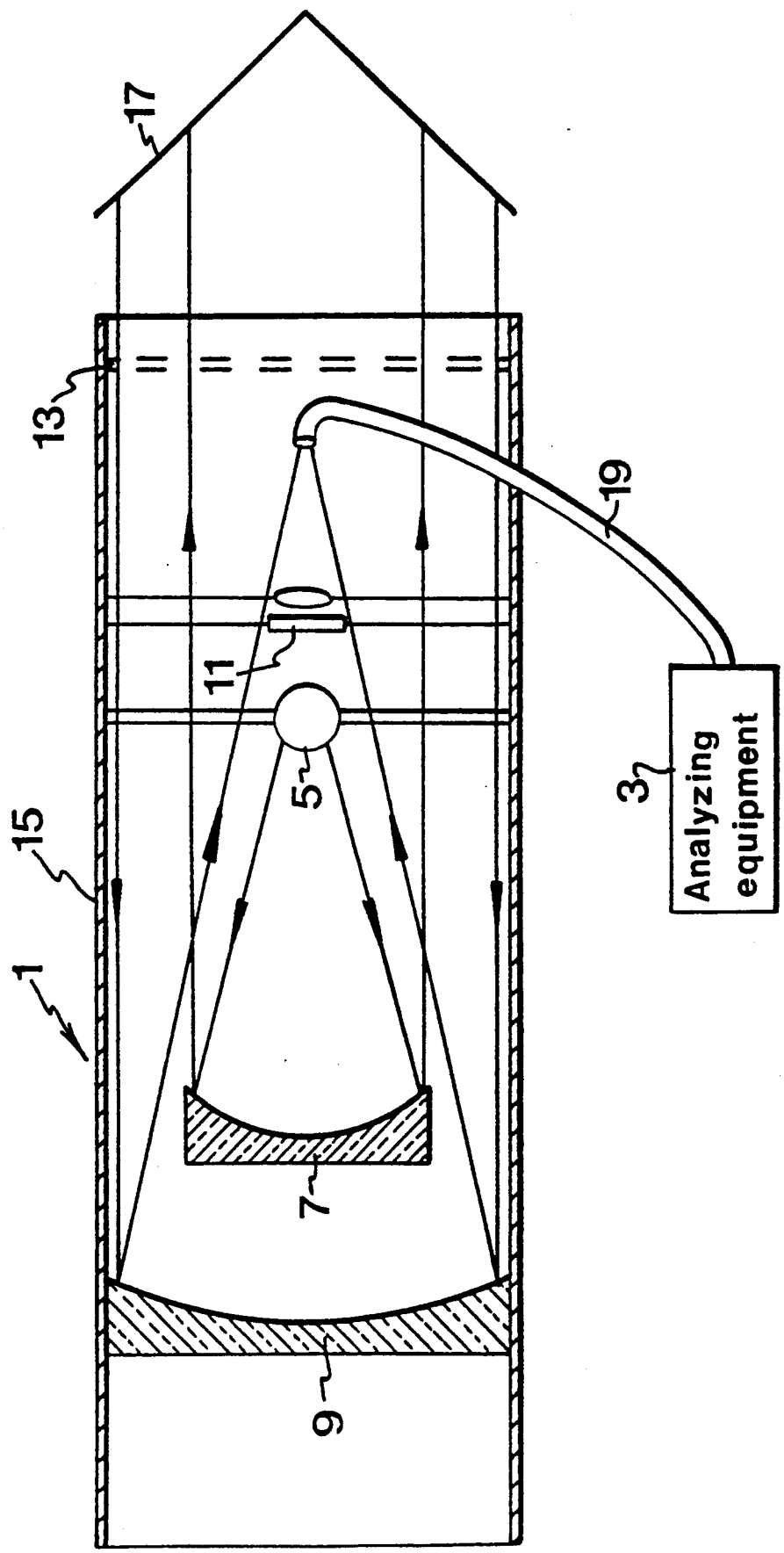

APPARATUS FOR EMITTING AND RECEIVING LIGHT

BACKGROUND OF THE INVENTION

1. Field of the Invention

The present invention relates to an apparatus for emitting and receiving light, said apparatus comprising an emitter with a spectrally broadband light source and a concave first mirror in the focus of which said light source is positioned, and a receiver which is adapted to receive light emitted from the light source and which is connected to equipment for analyzing the light received.

2. Description of Background Art

The paper "Differential optical absorption spectroscopy system used for atmospheric mercury monitoring", in Applied Optics, Vol. 25, No. 3, Feb. 1, 1986, reports on equipment for controlling air pollution by means of differential optical absorption spectroscopy. This equipment is chiefly made up of a device for emitting light, a device for receiving the light emitted, a spectrometer, a multi-channel analyser, and a computer. The device for emitting light (in the following called the emitter) comprises a spectrally broadband light source and a concave mirror in the focus of which the light source is positioned. The device for receiving the light emitted (in the following called the receiver) comprises a concave mirror and an inclined plane mirror which is arranged in the vicinity of the focus of the concave mirror and which reflects the received light to the input optics of the spectrometer. Emitter and receiver should be spaced apart a distance of from 10 m to 10 km.

When measuring air pollution by means of this equipment, a parallel light beam is emitted from the emitter to the receiver through the area in which the air pollution is to be measured. The light received is spectrally divided in the spectrometer and the resulting spectrum is fed to the multi-channel analyser and the computer by means of which the concentration C of different substances in the air between the emitter and the receiver can be determined on the basis of the Lambert-Beer law:

$$C = \log(I'_o/I)/(\epsilon L)^2$$

wherein

C is the concentration of a substance,
$I'_o$ is the light intensity without any differential absorption,
I is the light intensity depending on the absorption of the substance,
$\epsilon$ is the differential absorption cross-section of the substance, which is determined by calibration, and
L is the measuring distance.

The quotient $(I'_o/I)$ is determined by dividing the spectrum obtained from the spectrometer by a polynomial (first to fifth order) which is obtained by a least squares fit to the absorption spectrum.

However, the apparatus described is in some respects inadequate. First, it can only by used for differential measurings, which means that only the concentration of substances which absorb light at one or a few distinct wavelengths or wavebands can be determined. Thus, the concentrations of $Cl_2$, $H_2S$ and other substances which absorb light continuously or in broad wave length ranges cannot be determined by means of this equipment. In order to determine the concentration of these substances, total absorption measurings have to be effected.

Second, the receiver is difficult to mount because it has to be fixed in a highly exact position so that the light can be reflected to the plane mirror and further to the input optics of the spectrometer. In some weather conditions, the receiver may be dislocated and require adjustment.

Third, there has to be two power supplies, one for the emitter and one for the receiver.

Fourth, it is difficult in narrow measuring spaces, e.g. in chimneys, to place the emitter and the receiver at a sufficient distance from one another to make the measuring distance long enough.

SUMMARY AND OBJECTS OF THE INVENTION

One object of the present invention is, therefore, to provide an apparatus for emitting and receiving light, which makes it possible to carry out not only differential measuring but also total absorption measuring.

Another object of the invention is to provide an apparatus for emitting and receiving light, in which the difficulties associated with the mounting and position adjustment of the receiver have been reduced.

A further object of the invention is to provide an apparatus for emitting and receiving light, in which only one power supply is needed.

Yet another object of the invention is to provide an apparatus for emitting and receiving light, which requires less space for achieving a given measuring distance.

These objects are achieved by means of an apparatus having the distinctive features stated in the appended claims.

With the aid of a shielding element, light solely from the light source and light having travelled the measuring distance from the emitter to the reflector unit, and back to the receiver, can alternately be fed to the spectrometer for analysis. In this manner, it becomes possible to determine a reference spectrum for the light source and, consequently, determine the total absorption, i.e. determine the light intensity without absorption, without executing the above curve fitting, which in its turn means that the concentrations of substances with broad absorption bands and continuous absorption spectra can be determined.

According to the invention, the emitter and the receiver are mounted adjacent to one another, and a reflector unit is used for reflecting the emitted light towards the receiver. The position adjustment of the reflector unit is far less critical than that of the receiver described in the above article, since the reflector reflects the light in the same direction as it was received within a narrow range. Furthermore, the receiver is easily accessible for position adjustment, an operation which, furthermore, may be automated.

Also, only one power supply is needed since the emitter and the receiver are arranged adjacent to one another.

Furthermore, to produce a given measuring distance, only half the distance is needed between the emitter/-receiver and the reflector unit in the apparatus according to the invention, compared with the distance between the emitter and the receiver in the above-mentioned paper.

The apparatus according to the invention is advantageous also in that the emitter/receiver can be movably mounted on a shaft, and a number of reflector units can be mounted in different directions so that the measuring can be carried out in different directions with only one equipment. Thus, a more complete picture of, for instance, the extent of air pollution in an area can be obtained.

BRIEF DESCRIPTION OF THE DRAWING

The present invention will be illustrated below by means of an embodiment, reference being had to the accompanying drawing:

The FIGURE is a schematic longitudinal section of an apparatus 1 for emitting and receiving light, said apparatus being connected to an analysing equipment 3 which is only shown as a box.

DETAILED DESCRIPTION OF THE PREFERRED EMBODIMENTS

The apparatus 1 comprises a light source 5, a concave first mirror 7, a concave second mirror 9, a first shielding element 11, a second shielding element 13, all of which are mounted in a tube 15, and a retroreflector unit 17. The apparatus 1 is connected to the analysing equipment 3 by means of an optical fibre 19.

The light source 5 consists of a spectrally broadband xenon lamp which is positioned in the focus of the first mirror 7, the lamp and the mirror together forming the emitter. The diameter of the first mirror 7 is 100 mm, and its focal length is 60 cm.

The second mirror 9, which forms the receiver, is mounted behind the first mirror 7, relative to the lamp 5. The focal length of the second mirror is 90 cm, its diameter is 150 mm, and one end of the optical fibre 19 is positioned in its focus.

The mirrors may, of course, have other diameters and focal lengths than those stated above on condition that the periphery of the second mirror 9 is situated outwardly of the periphery of the first mirror 7 so as to be capable of receiving the light from the reflector 17, and on condition that the focus of the second mirror 9 is located in front of the lamp.

The first shielding element 11 is positioned between the lamp 5 and the optical fibre 19 so close to the lamp that it does not prevent the light reflected by the second mirror from reaching the optical fibre. The shielding element 11 comprises a shield which is mounted on a shaft and is movable from a first position in which the shield prevents the light emitted by the lamp from reaching the optical fibre directly, and a second position in which the shield is turned aside so that the light from the lamp can be directly received by the optical fibre. A convex lens can be provided behind the first shielding element 11 for focussing the light from the lamp to the optical fibre 19 when the shield 11 is turned aside.

The second shielding element 13, which is only shown schematically, is positioned between the optical fibre 19 and the front end of the tube 15. Like the first shielding element 11, the second shielding element 13 consists of a shield which is mounted on a shaft and is movable between two positions. In the first position, the shield is turned aside so as to allow light to pass out of and into the tube 15. In the second position, the shield prevents the light from the retroreflector 17 from reaching the optical fibre. The second position is used when the reference spectrum of the lamp is to be established. Instead of having a shield which is made to block the tube, said tube may be turned away from the retroreflector unit.

Preferably, the retroreflector unit 17 comprises twelve to sixteen juxtaposed retroreflectors. Since these reflectors are already known and commercially available, they need not be described in detail.

The apparatus operates as follows. In differential measuring, the light is emitted from the emitter 5, 7 towards the retroreflector unit 17 which reflects the light towards the receiver 9. Owing to dispersion, the light beam will have a larger diameter after having travelled the measuring distance from the emitter to the receiver, for which reason the light will impinge upon the second mirror 9 in the area outwardly of the periphery of the mirror 7. From there, the light is reflected towards the optical fibre 19 from which it is further conducted to the analyzing equipment. In differential measuring, the shielding element 11 is all the time maintained in the first position in which the direct light from the lamp is shielded off. Naturally enough, the second shielding element 13 is in the first position permitting the light to pass. The concentration is determined in the above manner.

In total absorption measuring, a reference spectrum for the lamp 5 is first established. To this end, the second shielding element 13 is moved to the second position in which it shuts off the light from the retroreflector unit, and the first shield element 11 is turned aside so that the optical fibre directly receives the light from the lamp. When the reference spectrum has been established, the shielding elements are moved to their opposite positions and measuring is effected as in differential measuring. When the concentration is to be established, the Lambert-Beer law is, as before, used, but the quotient $I'_o/I$ is replaced by the quotient of the reference spectrum and the absorption spectrum obtained, while the differential absorption cross-section is replaced by the total absorption cross-section of the substance at issue.

It goes without saying that the described embodiment of the invention is only an example that can be varied within the scope of the appended claims. Although the description of the apparatus focusses on the determination of concentrations, the apparatus may, of course, also be used for determining other parameters. Furthermore, the apparatus is not restricted to measuring concentrations in air; it may also be used for measuring in other gases or in liquids.

We claim:

1. An apparatus for emitting and receiving light, comprising an emitter with a light source (5) and a concave mirror (7) in the focus of which said light source is positioned, and a receiver (9) which is adapted to receive light emitted from the light source and which is connected to equipment (3) for analyzing the light received, characterised in that the receiver comprises a concave mirror (9) which is disposed behind the mirror (7) of the emitter, relative to the light source (5), and whose periphery is situated outwardly of the periphery of the mirror (7) and whose focus, in which a means (19) for transmitting the received light to the analysing equipment (3) is provided, is located in front of the light source (5), and that the apparatus further comprises a reflector unit (17) adapted to reflect the light from the emitter to the receiver, and a movable first shielding element (11) adapted to prevent, in a first position, the light from the light source from reaching the transmitter directly and to let through, in a second position, the light from the light source directly to the transmitter (19).

2. Apparatus as claimed in claim 1, characterised by a convex lens which is provided between said shielding element and the transmitter (19) and in one focus of which said transmitter (19) is positioned.

3. Apparatus as claimed in claim 1 or 2, characterised by a second shielding element (13) provided between the transmitter (19) and the reflector (17) and adapted to prevent, when the movable first shielding element (11) is in the second position, light reflected by the reflector from reaching said transmitter.

4. Apparatus as claimed in claim 1 or 2, characterised in that the reflector unit (17) comprises retroreflectors.

* * * * *